(12) United States Patent
Taneda

(10) Patent No.: US 11,062,735 B2
(45) Date of Patent: Jul. 13, 2021

(54) RADIATION IMAGE DISPLAY APPARATUS AND RADIATION IMAGE PHOTOGRAPHING SYSTEM

(71) Applicant: Konica Minolta, Inc., Tokyo (JP)

(72) Inventor: Atsushi Taneda, Koganei (JP)

(73) Assignee: Konica Minolta, Inc., Tokyo (JP)

(*) Notice: Subject to any disclaimer, the term of this patent is extended or adjusted under 35 U.S.C. 154(b) by 64 days.

(21) Appl. No.: 15/902,353

(22) Filed: Feb. 22, 2018

(65) Prior Publication Data

US 2018/0277159 A1    Sep. 27, 2018

(30) Foreign Application Priority Data

Mar. 22, 2017 (JP) .............................. JP2017-055288

(51) Int. Cl.
*G11B 27/00* (2006.01)
*G01T 1/17* (2006.01)
(Continued)

(52) U.S. Cl.
CPC .............. *G11B 27/007* (2013.01); *A61B 6/00* (2013.01); *A61B 6/4405* (2013.01); *A61B 6/461* (2013.01);
(Continued)

(58) Field of Classification Search
CPC G11B 27/007; G01T 1/17; A61B 6/00; A61B 6/4405; A61B 6/461; A61B 6/4283;
(Continued)

(56) References Cited

U.S. PATENT DOCUMENTS

2002/0064315 A1* 5/2002 Spahn ................ H04N 5/23293
382/299
2003/0081734 A1* 5/2003 Nicolas ................ A61B 6/0457
378/205
(Continued)

FOREIGN PATENT DOCUMENTS

JP     2006296926 A    11/2006
JP     20170172558 A    8/2010
(Continued)

OTHER PUBLICATIONS

Takemura et al.—JP 2012-095831 A—English—Google Patents obtained Sep. 27, 2019 (Year: 2019).*
(Continued)

*Primary Examiner* — David P Porta
*Assistant Examiner* — Jeremy S Valentiner
(74) *Attorney, Agent, or Firm* — Osha Bergman Watanabe & Burton LLP

(57) ABSTRACT

A radiation image display apparatus that includes: a hardware processor that generates the moving image for preview based on the pieces of image data of the plurality of frames obtained by moving image photographing of an object with radiation; and a holder that holds the moving image, wherein the hardware processor further: performs reproduction control on the moving image, performs image adjustment on the moving image, displays the moving image on the display during photographing the moving image, and displays the moving image according to the reproduction control or the moving image subjected to the image on the display.

19 Claims, 11 Drawing Sheets

(51) Int. Cl.
*A61B 6/00* (2006.01)
*G06F 3/0485* (2013.01)
*G06F 3/0488* (2013.01)
*G06F 3/0484* (2013.01)
*G06F 3/0354* (2013.01)
*G03B 42/04* (2021.01)

(52) U.S. Cl.
CPC .............. *G01T 1/17* (2013.01); *A61B 6/4283* (2013.01); *G03B 42/04* (2013.01); *G06F 3/03543* (2013.01); *G06F 3/0485* (2013.01); *G06F 3/0488* (2013.01); *G06F 3/04847* (2013.01)

(58) Field of Classification Search
CPC ............... G03B 42/04; G06G 3/03543; G06G 3/04847; G06G 3/0485; G06G 3/0488
See application file for complete search history.

(56) References Cited

U.S. PATENT DOCUMENTS

| | | | |
|---|---|---|---|
| 2012/0145914 A1* | 6/2012 | Yamamichi | G01T 1/17 250/393 |
| 2013/0259203 A1* | 10/2013 | Ishizaka | H05G 1/64 378/98.2 |
| 2016/0081642 A1* | 3/2016 | Okusu | G06F 3/0482 378/62 |
| 2016/0120495 A1* | 5/2016 | Miyazawa | A61B 6/54 378/21 |
| 2017/0134605 A1* | 5/2017 | Ju | G06F 3/04817 |
| 2017/0360390 A1* | 12/2017 | Tajima | A61B 6/00 |

FOREIGN PATENT DOCUMENTS

| | | | |
|---|---|---|---|
| JP | 2010-268979 A | | 12/2010 |
| JP | 2010268979 A | * | 12/2010 |
| JP | 2012095831 A | * | 5/2012 |
| JP | 2012-120724 A | | 6/2012 |
| JP | 2013226243 A | | 11/2013 |
| JP | 2016112212 A | | 6/2016 |
| JP | 2016198277 A | | 12/2016 |

OTHER PUBLICATIONS

Muraoka et al.—JP 2010-268979 A—English—Google Patents obtained Sep. 27, 2019 (Year: 2019).*
Office Action issued in the counterpart Japanese Patent Application No. 2017-055288, dated Jun. 23, 2020 (11 pages).
Office Action issued in the counterpart Japanese Patent Application No. 2017-055288, dated Dec. 22, 2020 (6 pages).

* cited by examiner

| D(1,1) | D(1,2) | D(1,3) | D(1,4) | D(1,5) | |
|---|---|---|---|---|---|
| D(2, 1) | D(2, 2) | D(2, 3) | D(2, 4) | D(2, 5) | |
| D(3, 1) | D(3, 2) | D(3, 3) | D(3, 4) | D(3, 5) | |
| D(4, 1) | D(4, 2) | D(4, 3) | D(4, 4) | D(4, 5) | |
| D(5, 1) | D(5, 2) | D(5, 3) | D(5, 4) | D(5, 5) | |
| D(6, 1) | D(6, 2) | D(6, 3) | D(6, 4) | D(6, 5) | |
| D(7, 1) | D(7, 2) | D(7, 3) | D(7, 4) | D(7, 5) | |
| D(8, 1) | D(8, 2) | D(8, 3) | D(8, 4) | D(8, 5) | |
| D(9, 1) | D(9, 2) | D(9, 3) | D(9, 4) | D(9, 5) | |
| D(10, 1) | D(10, 2) | D(10, 3) | D(10, 4) | D(10, 5) | |
| D(11, 1) | D(11, 2) | D(11, 3) | D(11, 4) | D(11, 5) | |
| D(12, 1) | D(12, 2) | D(12, 3) | D(12, 4) | D(12, 5) | |

RADIATION IMAGE DISPLAY APPARATUS AND RADIATION IMAGE PHOTOGRAPHING SYSTEM

The entire disclosure of Japanese patent Application No. 2017-055288, filed on Mar. 22, 2017, is incorporated herein by reference in its entirety.

BACKGROUND

Technological Field

The present invention relates to a radiation image display apparatus and a radiation image photographing system.

Description of the Related Art

There is a radiation image photographing apparatus (also referred to as a flat panel detector, a semiconductor image sensor, or the like) that includes a plurality of radiation detecting elements arranged two-dimensionally (in a matrix) and detects radiation having transmitted through an object by converting the radiation to image data according to the intensity of the radiation by each of the radiation detecting elements (i.e., in each pixel). Such a radiation image photographing apparatus has been conventionally developed for so-called still image photographing (also referred to as plain radiography and the like) in which radiation image photographing is performed by irradiation through an object only once.

However, a radiation image photographing apparatus can store image data read from each radiation detecting element in a storage in the apparatus and can also transfer the image data to an external device. Thus, in recent years, a technique of photographing a moving image of a region to be photographed of a patient as an object by irradiating the radiation image photographing apparatus with radiation a plurality of times (or by sequential irradiation of the radiation image photographing apparatus with radiation and performing a reading process of image data by the radiation image photographing apparatus plurality of times) has been developed.

Moving image photographing includes, for example, dynamic photographing for photographing frame images by irradiating the chest of a patient, who is an object, as a region to be photographed with radiation a plurality of times. In dynamic photographing, for example, as illustrated in FIG. 13, each frame image of the patient's lung field R at each time T ($T=t_0$ to $t_6$) can be obtained. Then, by analyzing the moving image, attempts have been made to find out the maximal inspiratory level, the maximal expiratory level, the expiratory phase, the inspiratory phase, and the like of the lung field R and also to perform analysis that can be used for diagnosis (for example, refer to JP 2010-268979 A).

Meanwhile, the radiation image photographing apparatus can transfer the read image data while moving image photographing as described above to an external device. Then, when the radiation image display apparatus receives image data (also referred to as thinned data to be described below) that has been transferred from the radiation image photographing apparatus, the radiation image display apparatus may perform simpler image processing on the image data than precise image processing performed to generate a moving image as a so-called main image to display a moving image for preview on the screen promptly.

With such a configuration, a photographer such as a radiological technician can view the moving image for preview displayed on the screen, so that the photographer can check the image to determine whether the object is properly photographed, whether re-photographing of an image is necessary, or the like in real time (that is, during moving image photographing).

Conventionally, many radiation image display apparatuses have been configured to, when a still image is photographed, generate a preview image of the still image and display the preview image on the screen, and subsequently perform a process to generate a still image as a main image automatically (for example, refer to JP 2012-120724 A). Therefore, it can be thought that even when a moving image is photographed, many radiation image display apparatuses each generate a moving image for preview and display the moving image for preview on the screen, and subsequently start a generation process of a moving image as a main image automatically as described above.

However, when a radiation image display apparatus is configured as described above, a photographer such as a radiological technician has to wait until the radiation image display apparatus generates a moving image as a main image and displays the moving image on the screen even in a case where the photographer wants to change the density of a moving image for preview to determine necessity of re-photographing an image (that is, increase or decrease values of whole image data), zoom in the image, or view the image by frame feed.

In this case, the photographer can not readily start reproduction control such as image adjustment of the moving image including change of the density of the moving image (moving image for preview or as a main image) and view of the moving image by frame feed. For this reason, the radiation image display apparatus is inconvenient for photographers to use.

In addition, during image check, possibility of re-photographing an image remains. There are cases where a photographer asks a patient to wait in the position and posture as he/she is until the photographer checks the image because it is burdensome for the photographer to position a patient over again. However, in such a case, if the photographer can not readily start image adjustment and reproduction control on the moving image and thus start of image check by the photographer is delayed as described above, the burden on the patient as an object is large.

SUMMARY

One or more embodiments of the present invention provide a radiation image display apparatus and a radiation image photographing system that allow a photographer such as a radiological technician who is a user to check an image early in moving image photographing with radiation, and thus reduce the burden on a patient.

According to one or more embodiments of the present invention, there is provided a radiation image display apparatus that generates a moving image for preview based on pieces of image data of a plurality of frames obtained by moving image photographing of an object with radiation and displays the moving image on a display. The apparatus includes: a hardware processor that generates the moving image for preview based on the pieces of image data of the plurality of frames; and a holder that holds the moving image for preview generated by the hardware processor, wherein the hardware processor further performs reproduction control on the moving image for preview, performs image adjustment on the moving image for preview, displays the moving image for preview held by the holder on the display during photographing the moving image for preview, and displays the moving image for preview according to the reproduction control by the hardware processor on the display or displays the moving image for preview on which the image adjustment has been performed by the hardware processor.

BRIEF DESCRIPTION OF DRAWINGS

The advantages and features provided by embodiments of the invention will become more fully understood from the detailed description given hereinbelow and the appended drawings which are given by way of illustration only, and thus are not intended as a definition of the limits of the present invention.

DETAILED DESCRIPTION

Hereinafter, a radiation image display apparatus and a radiation image photographing system according to one or more embodiments of the present invention will be described with reference to the drawings. However, the scope of the invention is not limited to the disclosed embodiments.

[Configuration of Radiation Image Photographing Apparatus]

Figure 1:
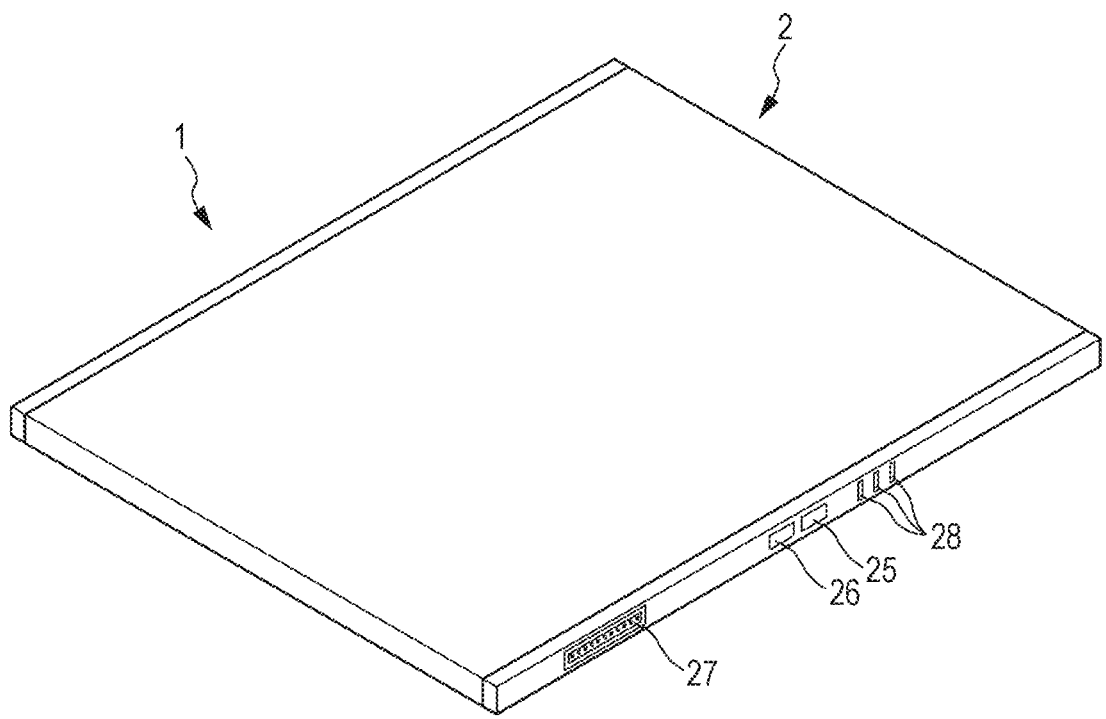
FIG. 1 is a perspective view illustrating the appearance of a radiation image photographing apparatus used in a radiation image photographing system according to one or more embodiments.
Figure 2:
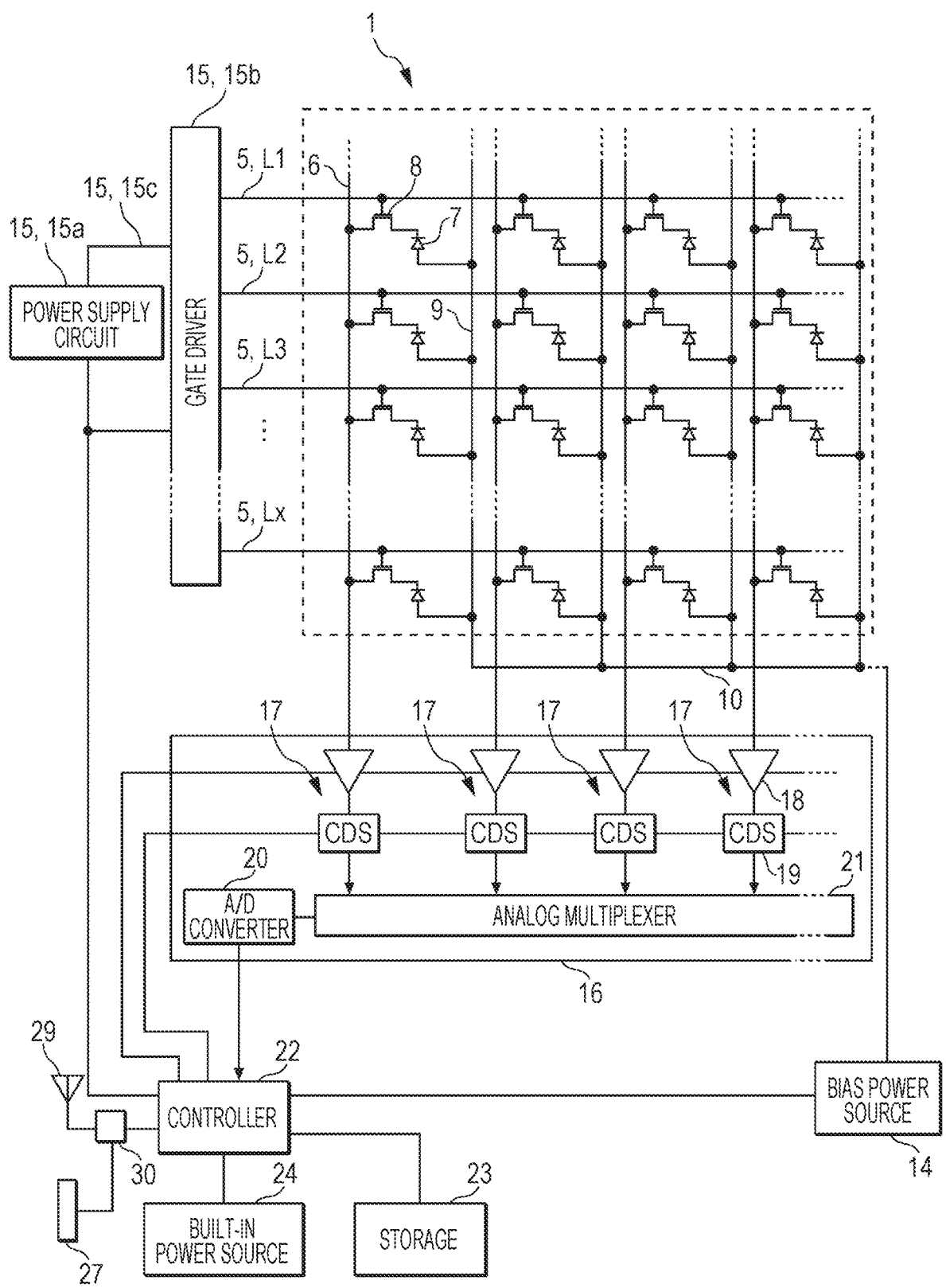
FIG. 2 is a block diagram illustrating an equivalent circuit of the radiation image photographing apparatus according to one or more embodiments of the invention.

Before describing a radiation image display apparatus and a radiation image photographing system according to one or more embodiments, a configuration of a radiation image photographing apparatus used in the radiation image photographing system according to one or more embodiments will be briefly described. In the following description, a radiation image photographing apparatus of so-called portable type, in which a sensor panel (not illustrated) is housed in a housing 2 (refer to FIG. 1 to be described below), will be described, but the present invention is not limited to this case and a radiation image photographing apparatus of so-called dedicated type (also referred to as installation type), in which a sensor panel is integrally formed with a support table or the like, may be used, for example FIG. 1 is a perspective view illustrating an appearance of a radiation image photographing apparatus, and FIG. 2 is a block diagram illustrating an equivalent circuit of the radiation image photographing apparatus. The radiation image photographing apparatus 1 is formed by housing a plurality of radiation detecting elements 7 in the housing 2 (refer to FIG. 1). The radiation detecting elements 7 is arranged two-dimensionally (in a matrix) on a sensor substrate (not illustrated) (refer to FIG. 2). As illustrated in FIG. 1, a power switch 25, a changeover switch 26, a connector 27, an indicator 28, and the like are disposed on one side surface of the housing 2 of the radiation image photographing apparatus 1. Although not illustrated in the drawing, an antenna 29 (refer to FIG. 2 to be described below) for communication with the outside in a wireless manner is provided on the opposite side surface of the housing 2.

As illustrated in FIG. 2, a bias line 9 is connected to each of the radiation detecting element 7, and a reverse bias voltage is applied to the radiation detecting elements 7 from a bias power source 14 via the bias line 9 and a connecting line 10 between the bias lines 9. A Thin Film Transistor (hereinafter referred to as TFT) 8 as a switch element is connected to each of the radiation detecting elements 7, and the TFT 8 is connected to a signal line 6. Each of the radiation detecting elements 7 is configured to generate electric charges corresponding to the dose of emitted radiation in the radiation detecting element 7.

In a scan driver 15, a gate driver 15b switches the on-voltage and the off-voltage supplied from a power supply circuit 15a via wiring 15c and applies the voltage to lines L1 to Lx of scanning lines 5. Each of the TFTs 8 is turned off when the off-voltage is applied thereto through the scanning line 5 to cut off conduction between the radiation detecting element 7 and the signal line 6, and accumulate electric charges in the radiation detecting element 7. Each of the TFTs 8 is turned on when the on-voltage is applied thereto through the scanning line 5, and releases the electric charges accumulated in the radiation detecting element 7 to the signal line 6.

Each signal line 6 is connected to corresponding one of readout circuits 17 in a readout IC 16. During a reading process of image data D, the on-voltage is sequentially applied to the lines L1 to Lx of the scanning lines 5 from the gate driver 15b. When each of the TFTs 8 is turned on, electric charges flow from the radiation detecting element 7 into the corresponding readout circuit 17 via the TFT 8 and the signal line 6, and a corresponding amplifying circuit 18 outputs a voltage value corresponding to the amount of electric charges flowed into the readout circuit 17. Each of correlated double sampling circuits (indicated as "CDSs" in FIG. 2) 19 is configured to read and output the voltage value output from the corresponding amplifying circuit 18 as a piece of analog value image data D. The pieces of output image data D are sequentially transmitted to an A/D converter 20 via an analog multiplexer 21, sequentially converted to pieces of digital value image data D by the A/D converter 20, and sequentially stored in a storage 23.

A controller 22 may include a computer, a Field Programmable Gate Array (FPGA), and the like, and the computer includes a Central Processing Unit (CPU), a Read Only Memory (ROM), a Random Access Memory (RAM), an input/output interface, and the like (not illustrated) that are connected to a bus. Alternatively, the controller 22 may be a dedicated control circuit.

To the controller 22, the storage 23 including a Static RAM (SRAM), a Synchronous DRAM (SDRAM), a NAND flash memory or the like, and a built-in power source 24 including a lithium ion capacitor or the like are connected. In addition, a communication unit 30 for communication with the outside via the antenna 29 and the connector 27 in a wireless manner or a wired manner is connected. As described above, the controller 22 is configured to control application of reverse bias voltage from the bias power source 14 to each of the radiation detecting elements 7, and control operation of the scan driver 15, the readout circuits 17, and the like to perform the reading process of pieces of the image data D from the radiation detecting elements 7.

In one or more embodiments, when a moving image is photographed, the controller 22 is configured to read out a piece of the image data D for each frame, store the piece of image data D in the storage 23, and transfer the piece of the image data D to a radiation image display apparatus 60 (refer to FIGS. 3 and 4 to be described below) via the communication unit 30.

Note that the radiation image photographing apparatus 1 is configured to perform a reading process in a process sequence similarly to the reading process of the pieces of the image data D described above to read a piece of offset data 0 for each of the radiation detecting elements 7, and transfer the read piece of the offset data 0 to the radiation image display apparatus 60 before starting moving image photographing in a state where the radiation image photographing apparatus 1 is not irradiated with radiation.

[Radiation Image Photographing System]

Figure 3:
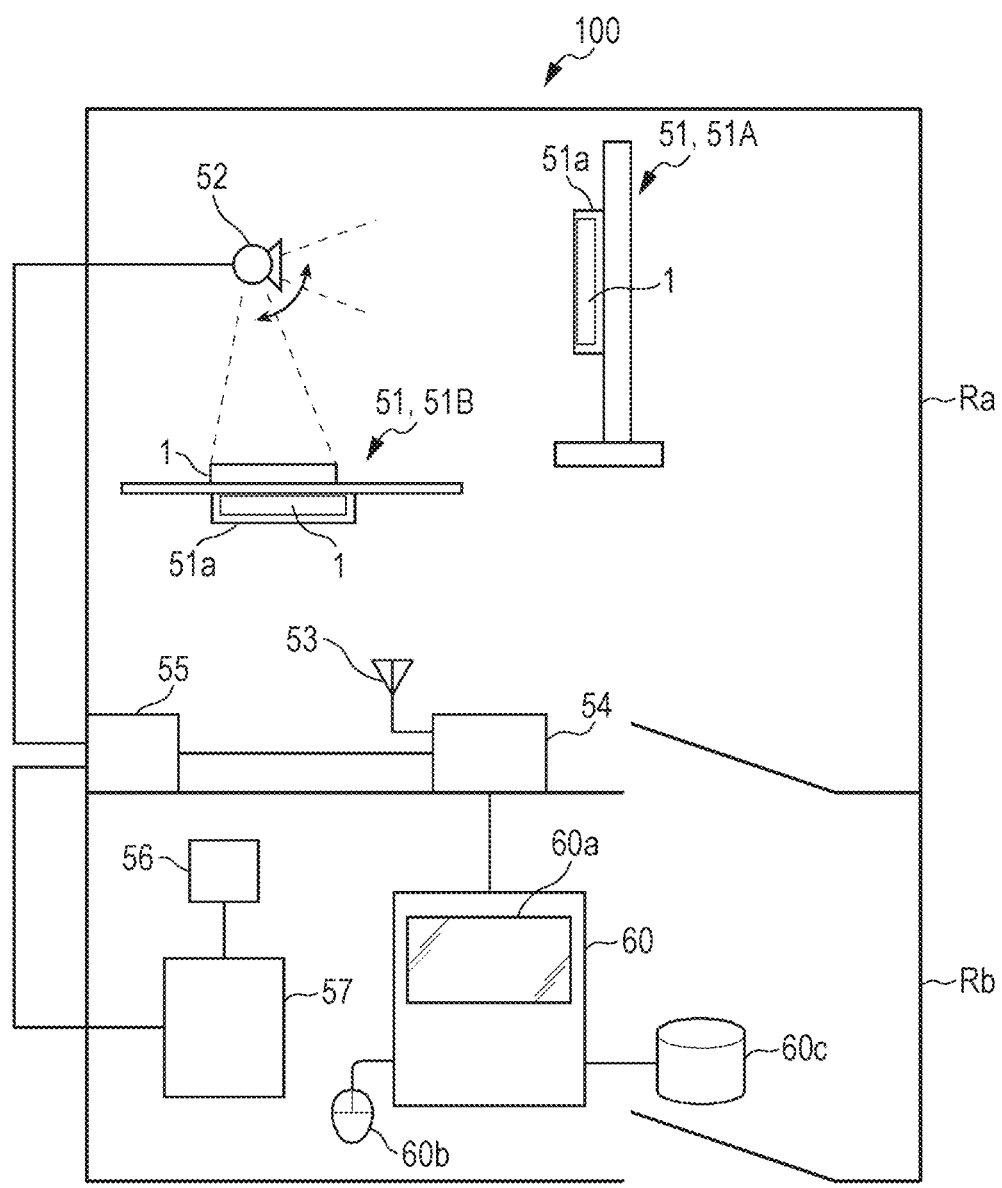
FIG. 3 is a diagram illustrating a configuration example of the radiation image photographing system according to one or more embodiments of the invention.
Figure 4:
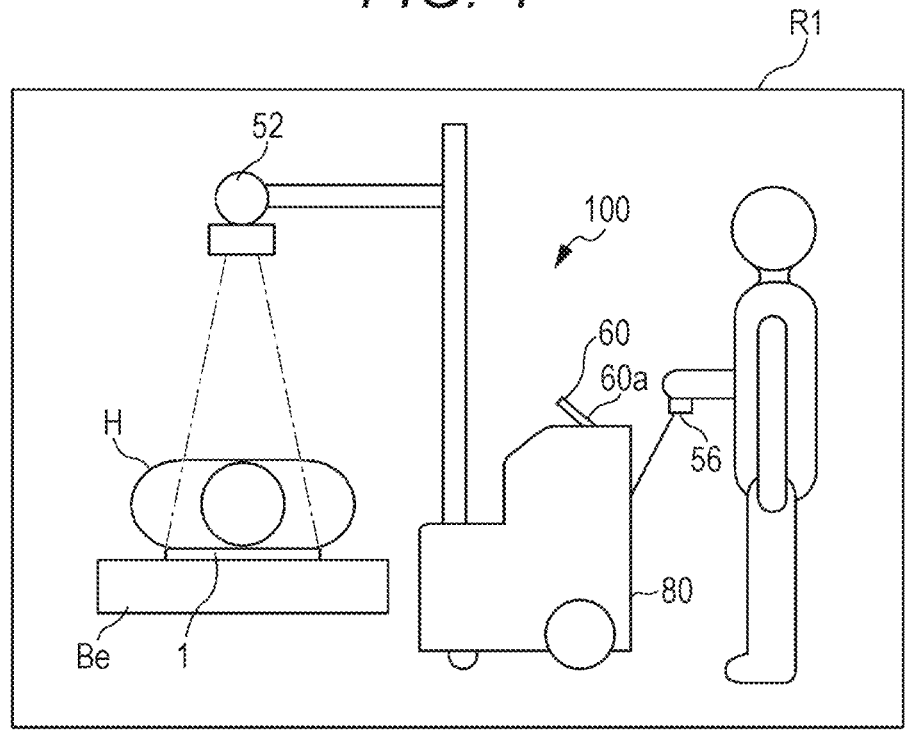
FIG. 4 is a diagram illustrating a configuration example of the radiation image photographing system configured on a visiting car according to one or more embodiments of the invention.

Next, the radiation image photographing system according to one or more embodiments will be described. As illustrated in FIG. 3, a radiation image photographing system 100 may be formed in a photographing room Ra or in a front room Rb, for example. Alternatively, the radiation image photographing system 100 may be mounted on a visiting car 80 as illustrated in FIG. 4.

For example, when the radiation image photographing system 100 is formed in the photographing room Ra or the like as illustrated in FIG. 3, the radiation image photographing apparatus 1 may be loaded on a cassette holder 51a of a photographing table 51 (a photographing table 51A for standing posture photographing or a photographing table 51B for lying posture photographing) and used for photographing. Alternatively, it is also possible to dispose the radiation image photographing apparatus 1, for example, by inserting the radiation image photographing apparatus 1 between an object (not illustrated) lying on a top plate of the photographing table 51B for photographing lying posture and the top plate.

In the photographing room Ra, at least one radiation irradiation apparatus 52 that irradiates an object (not illustrated) with radiation is provided. In addition, in the photographing room Ra, a relay 54 having an access point 53 for relaying wireless or wired communication and the like between apparatuses inside and outside the photographing room Ra is provided.

The relay 54 relays communication between the radiation image photographing apparatus 1 and the radiation image display apparatus 60. The relay 54 is also connected to a generator 55 of the radiation irradiation apparatus 52. The relay 54 incorporates a converter (not illustrated) that converts signals for Local Area Network (LAN) communication to be transmitted from the radiation image photographing apparatus 1 or the like to the generator 55 of the radiation irradiation apparatus 52 to a signal for the radiation irradiation apparatus 52 and also performs reverse conversion.

When a tube voltage, a tube current, an irradiation time (or mAs value), and the like are set by a photographer such as a radiological technician, the generator 55 of the radiation irradiation apparatus 52 is configured to perform various kinds of control on the radiation irradiation apparatus 52. For example, the radiation irradiation apparatus 52 is controlled to irradiate an object with a dose corresponding to the set tube voltage.

In the front room (also referred to as an operation room or the like) Rb, an operation console 57 of the radiation irradiation apparatus 52 is provided, and on the operation console 57, an exposure switch 56 that is operated by a photographer such as a radiological technician to instruct the generator 55 to start to irradiate an object with radiation is provided. In the front room Rb, the radiation image display apparatus 60 is installed.

The radiation image photographing system 100 can be configured by providing the radiation image display apparatus 60 outside the photographing room Ra and the front room Rb, in another room, or the like. The configuration and the like of the radiation image display apparatus 60 will be described below. In one or more embodiments, the radiation image display apparatus 60 also functions as a console for controlling the radiation image photographing apparatus 1 and the generator 55 of the radiation irradiation apparatus 52 to instruct the start of photographing, and the like. The radiation image display apparatus 60 and the console may be configured separately.

The radiation image display apparatus 60 is provided with a display 60a constituted of a Cathode Ray Tube (CRT), an Liquid Crystal Display (LCD) or the like, and an input unit 60b. In addition, to the radiation image display apparatus 60, a storage 60c constituted of a Hard Disk Drive (HDD) or the like is connected, or the radiation image display apparatus 60 incorporates the storage 60c.

In one or more embodiments, the input unit 60b is constituted of a mouse, a touch panel and the like. In the following, a case where a photographer inputs an instruction through mouse operation will be described. However, for example, a photographer can input an instruction through touch panel operation, in which a photographer touches a touch panel, or operation by a gesture of a photographer (that is, an operation of inputting an instruction by causing the input unit 60b to read a gesture of the photographer).

On the other hand, as described above, the radiation image photographing system 100 may be configured by mounting the radiation irradiation apparatus 52, the radiation image display apparatus 60, and the like on the visiting car 80, and the visiting car 80 may be carried into the patient room R1 or the like to perform photographing as illustrated in FIG. 4. Although not illustrated, in this case, the generator 55 of the radiation irradiation apparatus 52, the relay 54, and the like are housed in the main body of the visiting car 80.

In this case, as illustrated in FIG. 4, the radiation image photographing apparatus 1 is inserted between a bed Be and a patient as an object H, or is put on the patient's body when used for photographing Also in this case, photographing is performed by irradiating an object with radiation from the radiation irradiation apparatus 52 upon operation of the exposure switch 56 by a photographer such as a radiological technician.

Figure 5:
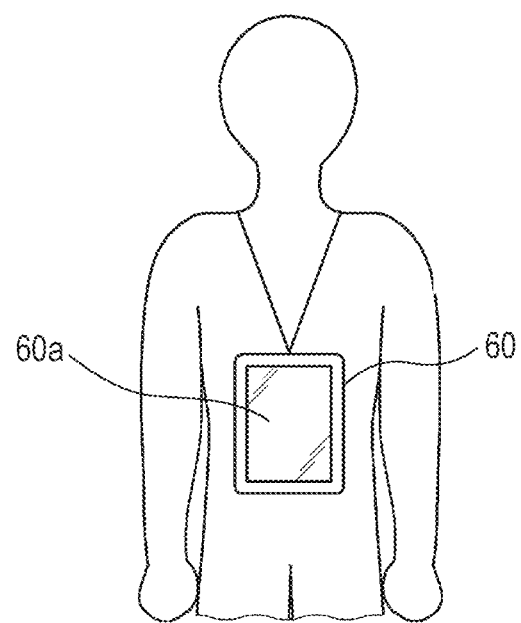
FIG. 5 is a diagram illustrating a configuration example of a portable terminal type radiation image display apparatus according to one or more embodiments of the invention.

Although the radiation image display apparatus 60 can be constituted of a desktop type or notebook type computer as illustrated in FIG. 3 or FIG. 4, for example as illustrated in FIG. 5, the radiation image display apparatus 60 of portable terminal type can be carried by a photographer such as a radiological technician.

Further, in the radiation image photographing system 100 according to one or more embodiments, moving image photographing is performed. As described above, in this case, moving image photographing can be performed by configuring the radiation image photographing system 100 such that the radiation irradiation apparatus 52 irradiates the radiation image photographing apparatus 1 a plurality of times through an object, and the radiation image photographing apparatus 1 performs the reading process of a piece of the image data D upon every irradiation, or the radiation irradiation apparatus 52 irradiates the radiation image photographing apparatus 1 through an object continuously, and the radiation image photographing apparatus 1 performs the reading process of a piece of the image data D a plurality of times.

In either case, the radiation image photographing apparatus 1 is configured to read radiation emitted through an object as a piece of the image data D for each frame, and transfer the read piece of the image data D to the radiation image display apparatus 60.

[Configuration and Operation of Radiation Image Display Apparatus]

Next, the radiation image display apparatus 60 according to one or more embodiments will be described. In one or more embodiments, it is assumed that the radiation image display apparatus 60 includes a general-purpose computer in which a CPU, a ROM, a RAM, an input/output interface, and the like (not illustrated) are connected to a bus, but the radiation image display apparatus 60 can be a dedicated apparatus. In one or more embodiments, as described above, when a piece of the image data D is transferred from the radiation image photographing apparatus 1 for each frame, the radiation image display apparatus 60 generates a moving image for preview based on the piece of the image data D and displays the moving image on the display 60a (refer to FIGS. 3 to 5).

Figures 6, 7:
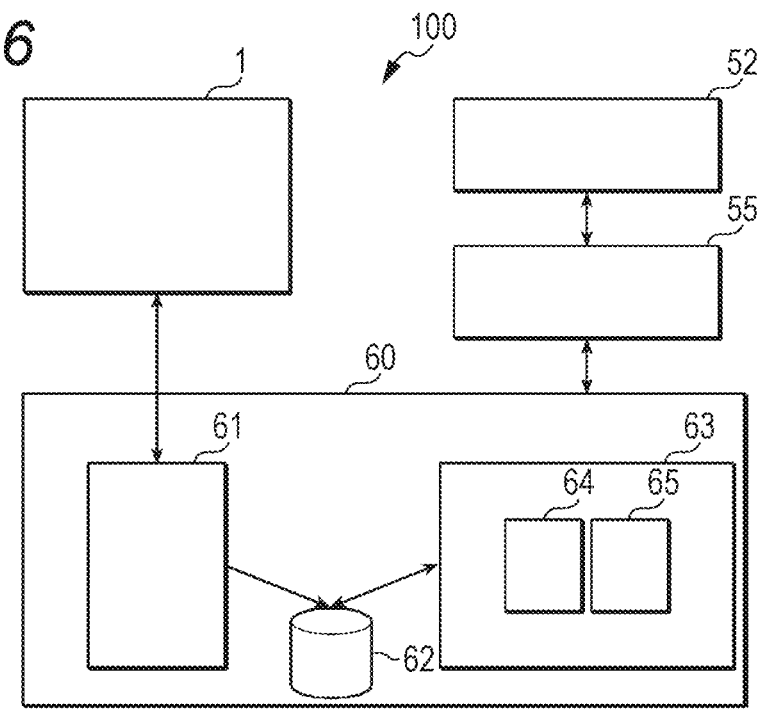
FIG. 6 is a block diagram illustrating a configuration of the radiation image display apparatus according to the embodiment according to one or more embodiments of the invention.
FIG. 7 is a view illustrating an example way to extract image data according to one or more embodiments of the invention.

FIG. 6 is a block diagram illustrating the configuration and the like of the radiation image display apparatus according to one or more embodiments. The radiation image display apparatus 60 includes a generator 61, a holder 62, a display unit 63, a reproduction controller 64, and an image adjuster 65.

When the image data D is transferred from the radiation image photographing apparatus 1 for each frame, the generator 61 generates a moving image for preview ppre (hereinafter, simply referred to as a preview image ppre) based on the image data D. Hereinafter, when the preview image ppre is referred, it may refer to frame images for preview of all frames, and may also refer to one frame image for preview.

In one or more embodiments, when generating the preview image ppre, the generator 61 generates the preview image ppre by performing simpler image processing than image processing performed to generate a moving image p as a main image (hereinafter simply referred to as a main image p, which includes a plurality of frame images) based on the image data D. However, when the performance of the radiation image display apparatus 60 has good performance and a high processing speed, the generator 61 can be configured to perform image processing that is as precise as image processing to generate the main image p also when generating the preview images ppre.

In one or more embodiments, the generator 61 is configured to generate the preview images ppre such that the preview image ppre are displayed on the display 60a at a frame rate lower than the frame rate in moving image photographing (that is, the frame rate when the radiation image photographing apparatus 1 performs the reading process of the image data D). In this case as well, when the radiation image display apparatus 60 has good performance and a high processing speed, the radiation image display apparatus 60 can be configured to display at a frame rate that is equal to the frame rate in moving image photographing.

When a frame rate of display is set lower than the frame rate in moving image photographing, the radiation image display apparatus 60 can be configured to simply lower the frame late. However, with such a configuration, real-time display of the preview image ppre can not be ensured. That is, if it is assumed that all the preview images ppre are displayed at a frame rate of display that is ½ of the frame rate in moving image photographing, it takes twice to display all the preview images ppre as long as the time required for moving image photographing even if display of the preview images ppre is started at the same time with the start of moving image photographing. Thus, the preview images ppre cannot be displayed in real time at the same time as moving image photographing.

Therefore, when the frame rate of display is set to a frame rate lower than the frame rate in moving image photographing, for example, when pieces of the image data D is transferred from the radiation image photographing apparatus 1 for respective frames, the generator 61 stores the pieces of image data D in a RAM or the like temporarily, extracts frames at a predetermined ratio (that is, a ratio of one frame every n frames (n is an integer of 2 or more)), and generates preview images ppre based on the pieces of the image data D of the extracted frames.

Then, the generated preview images ppre are displayed at a frame rate of 1/n of the frame rate in moving image photographing. Accordingly, the time required for displaying all the preview images ppre and the time required for photographing a moving image are the same, and it becomes possible to display the preview images ppre in real time at the same time as moving image photographing. Since the frame rate of display can be reduced to 1/n of the frame rate in moving image photographing in this manner, even the radiation image display apparatus 60 whose performance is not so good can display the preview images ppre in real time at the same time as moving image photographing by appropriately setting the above-described n.

For example, in a case where communication is performed between the radiation image photographing apparatus 1 and the radiation image display apparatus 60 (the relay 54 in the case of FIG. 3 and the like) in a wireless manner, the transfer speed of the image data D from the radiation image photographing apparatus 1 to the radiation image display apparatus 60 changes according to a degree of congestion and the like of a frequency band used in the wireless manner. When the transfer speed of the image data D from the radiation image photographing apparatus 1 to the radiation image display apparatus 60 is low, the rate of transferring the pieces of the image data D of photographed preview images ppre for frames becomes low even if the frame rate in moving image photographing is high. This makes a state that is substantially the same as a state where the frame rate of moving image photographing is lowered.

Then, when the transfer speed of the pieces of the image data D for frames becomes equal to or less than the frame rate of display in the radiation image display apparatus 60, a generation speed of preview images ppre is high enough to display the preview images ppre in real time based on pieces of the transferred image data D for all frames even when the radiation image display apparatus 60 does not extract frames at a predetermined ratio as described above. Thus, the radiation image display apparatus 60 can display the preview images ppre for all transferred pieces of image data D for frames in real time (that is, at the same time as moving image photographing).

Therefore, in the case where the radiation image display apparatus 60 is configured such that the generator 61 extracts frames from a plurality of frames at a predetermined ratio and generates preview images ppre based on pieces of the image data D of the extracted frames as described above, the radiation image display apparatus 60 can be configured to change a ratio of extracting frames (including a case where all frames are extracted) according to a transfer speed when pieces of image data D are transferred from the radiation image photographing apparatus 1 (that is, the transfer speed).

Instead of or in addition to lowering the frame rate of display of the preview images ppre than the frame rate in moving image photographing as described above, the radiation image display apparatus 60 can be configured such that the generator 61 extracts parts of a piece of image data D transferred from the radiation image photographing apparatus 1 for each frame at a predetermined ratio as illustrated in FIG. 7, and generates preview images ppre based on the extracted parts of image data D.

Even with such a configuration, it is possible to reduce the load of the generation process of the preview images ppre in the generator 61, and as in the case of extracting frames as described above, the processing speed of generation of the preview images ppre is improved. Thus, it is possible to generate and display preview images ppre at a higher frame rate and it becomes possible to display the preview images ppre in real time.

FIG. 7 illustrates a case where from pieces of image data D (n, m) of n rows and m columns, pieces of image data D (n, m) are extracted at a ratio of one row in every four rows as hatched in the drawing to form image data Dpre for preview as a way of extracting pieces of the image data D. In addition to this, it is also possible to extract pieces of image data D at a ratio of one piece from, for example, pieces of 3×3, 4×4, or the like of the image data D.

Each part of the radiation image display apparatus 60 according to one or more embodiments other than the generator 61 is configured as follows.

That is, the holder 62 (refer to FIG. 6) is configured to hold the preview images ppre generated by the generator 61 as described above. The holder 62 is constituted of a storage such as a RAM. The reproduction controller 64 is configured to perform reproduction control on the preview images ppre held by the holder 62, and the image adjuster 65 is configured to perform image adjustment on the preview images ppre.

The display unit 63 displays the preview images ppre generated by the generator 61 and held in the holder 62 on the display 60a (refer to FIGS. 3 to 5) at the same time as moving image photographing. In addition, the display unit 63 is configured to, after displaying the preview images ppre once as described above, display the preview images ppre on the display 60a according to the reproduction control of the reproduction controller 64, or display the preview images ppre on which the image adjustment has been performed by the image adjuster 65 on the display 60a.

In one or more embodiments, the generator 61 of the radiation image display apparatus 60 is configured to generate the preview images ppre based on the pieces of image data D for frames transferred from the radiation image photographing apparatus 1 and cause the holder 62 to hold the preview images ppre as described above, and upon completion of the generation process and the holding process, to sequentially and automatically (that is, without instruction from a photographer or the like) perform precise image processing on the pieces of image data D of frames to generate a main image p (that is, a moving image p as a main image).

In addition, when the generator 61 generates the main image p as described above, the display unit 63 of the radiation image display apparatus 60 displays the generated main image p on the display 60a instead of the preview images ppre having been displayed on the display 60a. This is because a photographer can check an image based on the main image p instead of the preview images ppre when the main image p is generated although one or more embodiments of the invention and allows a photographer to check an image early through reproduction control or image adjustment of preview images ppre to be described below.

However, if the preview images ppre are switched to the main image p while a photographer performs reproduction control or image adjustment on the preview images ppre, operation of reproduction control or image adjustment performed on the preview images ppre may be wasted. Therefore, even when the display unit 63 is configured as described above, the display unit 63 may be configured, for example, to keep displaying the preview images ppre and not to switch the preview images to the main image p while a photographer performs a reproduction control process or an image adjustment process on the preview images ppre.

[Actions of Radiation Image Display Apparatus and Radiation Image Photographing System According to One or More Embodiments]

Figure 8:
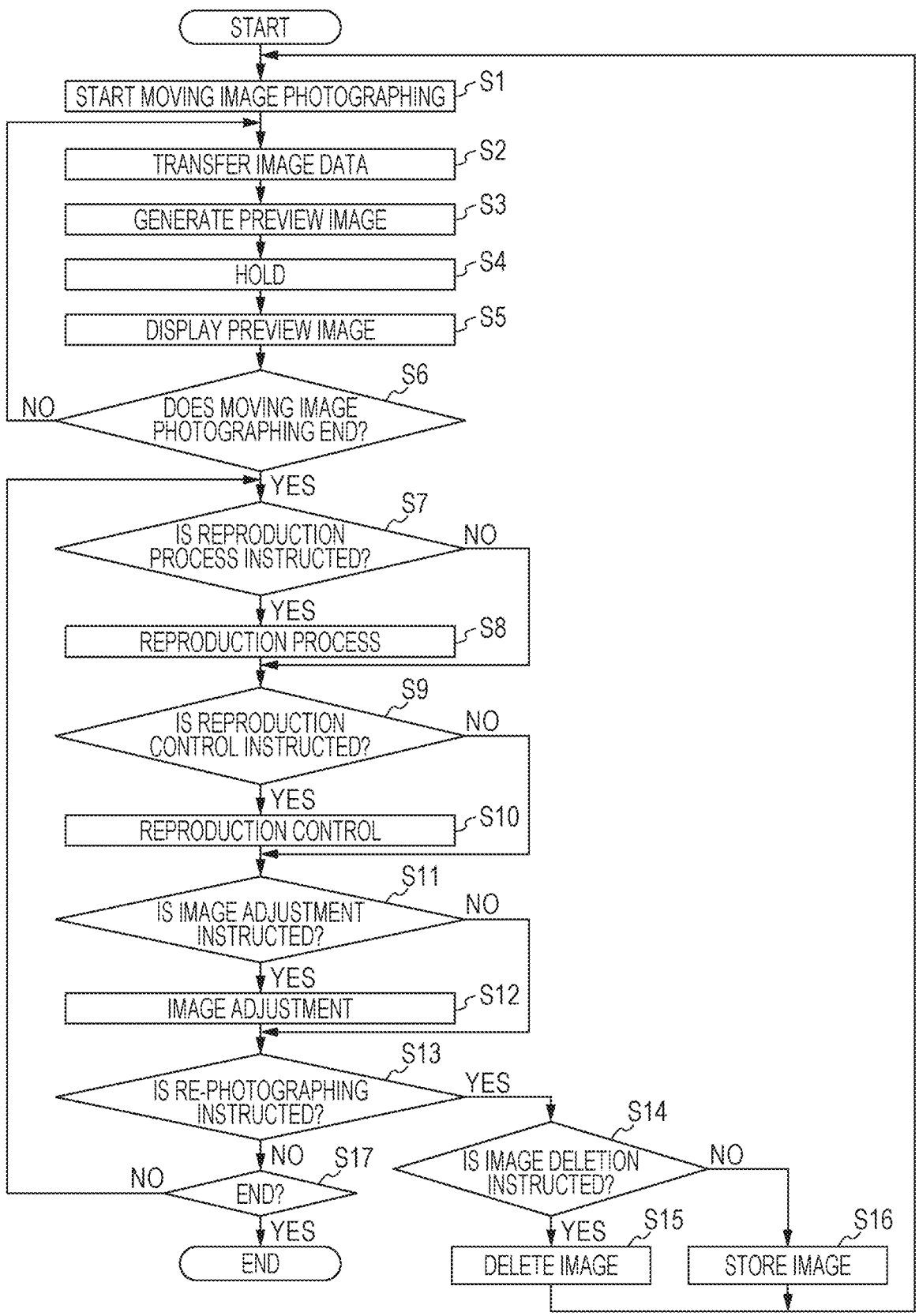
FIG. 8 is a flowchart for illustrating a flow of processes in the radiation image display apparatus and the radiation image photographing system, according to one or more embodiments of the invention.

Hereinafter, operation of the radiation image display apparatus 60 and the radiation image photographing system 100 according to one or more embodiments will be described. Based on a flowchart illustrated in FIG. 8, and the like, processes of the display unit 63, the reproduction controller 64, and the image adjuster 65 of the radiation image display apparatus 60 will be mainly described.

When the radiation image display apparatus 60 (console) transmits an instruction to start moving image photographing to the radiation image photographing apparatus 1, the generator 55 of the radiation irradiation apparatus 52, or the like based on operation of a photographer such as a radiological technician (step S1), emission of radiation from the radiation irradiation apparatus 52 is started, and the radiation image photographing apparatus 1 starts the reading process of the image data D, and starts moving image photographing.

Then, when a piece of the image data D is transferred from the radiation image photographing apparatus 1 for each frame (step S2), the generator 61 of the radiation image display apparatus 60 generates a preview image ppre (that is, a moving image for preview ppre) based on the transferred piece of image data D as described above (step S3). The holder 62 holds the preview image ppre generated by the generator 61 (step S4).

Then, the display unit 63 of the radiation image display apparatus 60 displays the preview images ppre held by the holder 62 on the display 60a (step S5) to display the preview images ppre in real time during moving image photographing. That is, in one or more embodiments, as described above, when the generator 61 generates a moving image for preview ppre during moving image photographing, and the generated moving image ppre is held by the holder 62 as described above, the display unit 63 reads the moving image for preview ppre from the holder 62 and displays the moving image ppre on the display 60a during moving image photographing. In this way, the first display of the preview image ppre, that is, so-called live display is performed. Then, the generator 61, the holder 62, and the display unit 63 continue the above processes until the moving image photographing ends (No in step S6).

In one or more embodiments, while a photographer operates the exposure switch 56 (refer to FIG. 3 and FIG. 4) of the radiation irradiation apparatus 52, the radiation irradiation apparatus 52 irradiates an object, and when the photographer stops operation of the exposure switch 56, radiation is stopped so that moving image photographing ends. However, it is also possible to set the number of irradiation or irradiation time from the radiation irradiation apparatus 52 in advance, and moving image photographing automatically ends when the set number of irradiation is reached or the wet irradiation time elapses.

Figure 9:
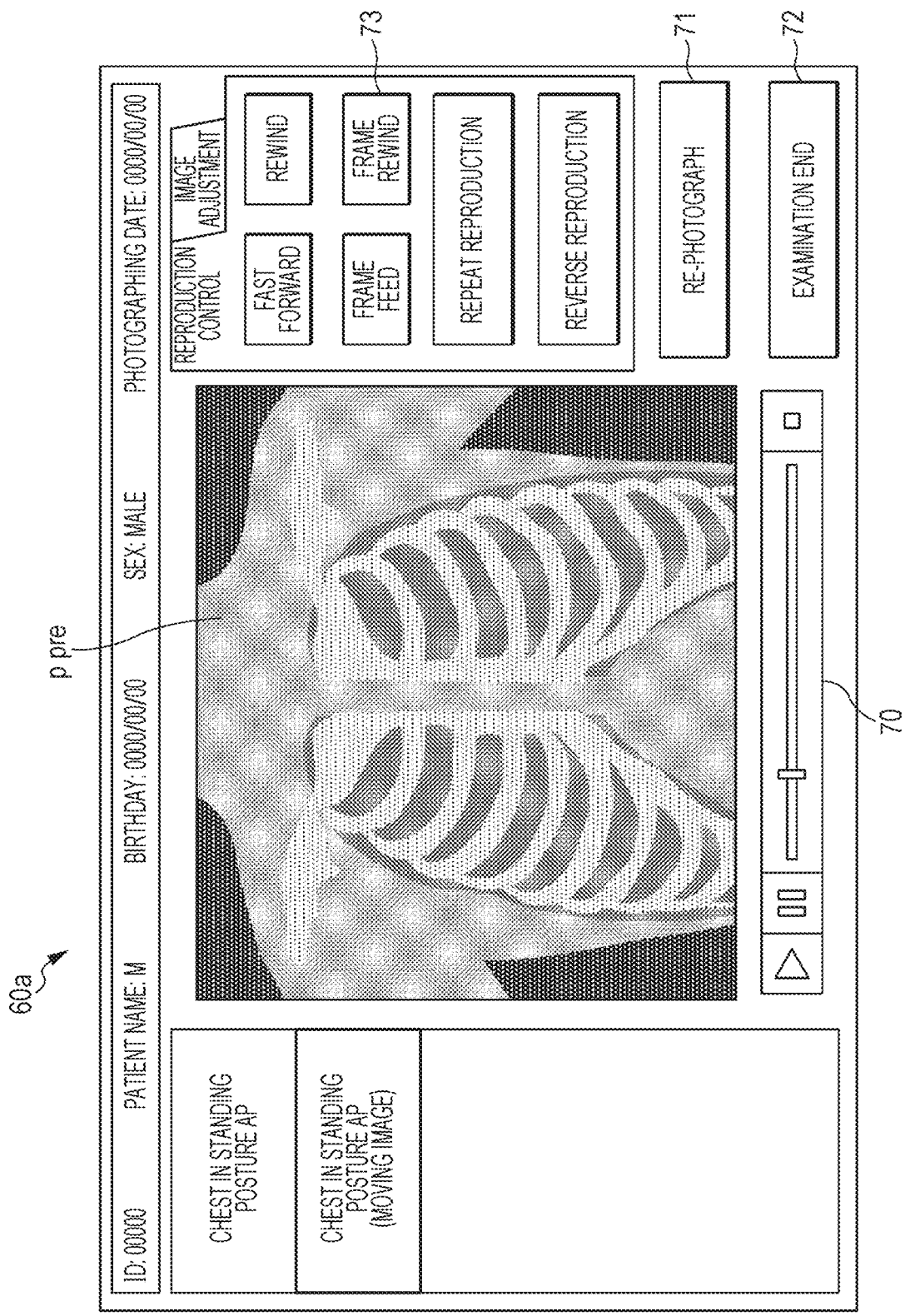
FIG. 9 is a view illustrating an example of a display screen displayed on a display of the radiation image display apparatus, and illustrating a case where a screen for reproduction control is displayed according to one or more embodiments of the invention.

When the moving image photographing ends (Yes in step S6) or when the preview images ppre are displayed during moving image photographing, the display unit 63 of the radiation image display apparatus 60 displays, for example, a display screen illustrated in FIG. 9 on the display 60a. At the center of the display screen, a preview image ppre is displayed. Below the preview image ppre, an operation part 70 including icons, a seek bar, and the like representing play, temporary stop, stop, etc. is displayed.

Then, when the photographer instructs a reproduction process by clicking one of the icons or moving a slider of the seek bar (Yes in step S7), the display unit 63 performs a reproduction process to playback the preview images ppre, temporarily stop the playback, stop the playback, start playback from a preview image ppre corresponding to the position of the slider moved by the photographer, or the like according to the instruction by the photographer (step S8).

In one or more embodiments, the process of reproducing the preview images ppre according to the operation of the icons or the slider of the seek bar displayed below the preview image ppre by a photographer is referred to as a reproduction process, and described separately from reproduction control by the reproduction controller 64 to be described below. In addition, the display unit 63 can be configured to start the reproduction process to reproduce preview images ppre automatically (that is, without instruction of the reproduction process by a photographer) at the time when the moving image photographing ends (Yes in step S6) as described above.

Meanwhile, the photographing conditions are displayed on the left side of the display screen, and the photographing conditions corresponding to the preview images ppre displayed in the center of the screen (in the case of FIG. 9, "chest in standing posture AP (moving image)") is displayed in highlight. Tabs for reproduction control and image adjustment are displayed on the right side of the display screen, and in one or more embodiments, it is possible to switch between reproduction control and image adjustment using the tabs. It is to be noted that FIG. 9 illustrates a case where a screen for reproduction control is displayed. In the lower right part of the display screen, a re-photograph icon 71 for inputting re-photographing instruction and an examination end icon 72 to be clicked when all processes are finished are displayed.

In one or more embodiments, as illustrated in FIG. 9, when the screen is switched to the reproduction control screen using the tabs, various icons 73 for reproduction control, that is, fast forward, rewind, frame feed, frame rewind, repeat playback of playback and reverse playback are displayed. Then, by clicking these icons 73, the photographer can input instructions to perform processes including fast forward, rewind, frame feed, frame rewind, repeat playback, and reverse playback. By clicking a play icon on the operation part 70 in this state, the normal reproduction process can be performed, and by clicking a stop icon, reproduction can be stopped.

Then, when the photographer instructs the reproduction control by clicking the icons 73 or clicking the icons on the operation part 70 (Yes in step S9), the reproduction controller 64 of the radiation image display apparatus 60 performs the reproduction control according to the instruction by the photographer (that is, fast forward etc.) (step S10).

In the above description, the reproduction controller 64 performs the reproduction control such as fast forward according to input from a user such as a radiological technician. However, a way of reproduction control can be previously set in the reproduction controller 64, and the reproduction controller 64 can be configured to perform the reproduction control including one or more of playback, reverse playback, stop, fast forward, rewind, frame feed, frame rewind, and repeat playback on the preview images ppre according to the preset way.

Then, the display unit 63 of the radiation image display apparatus 60 is configured to display the preview images ppre on the display 60a according to the reproduction control such as fast forward by the reproduction controller 64.

Figure 10:
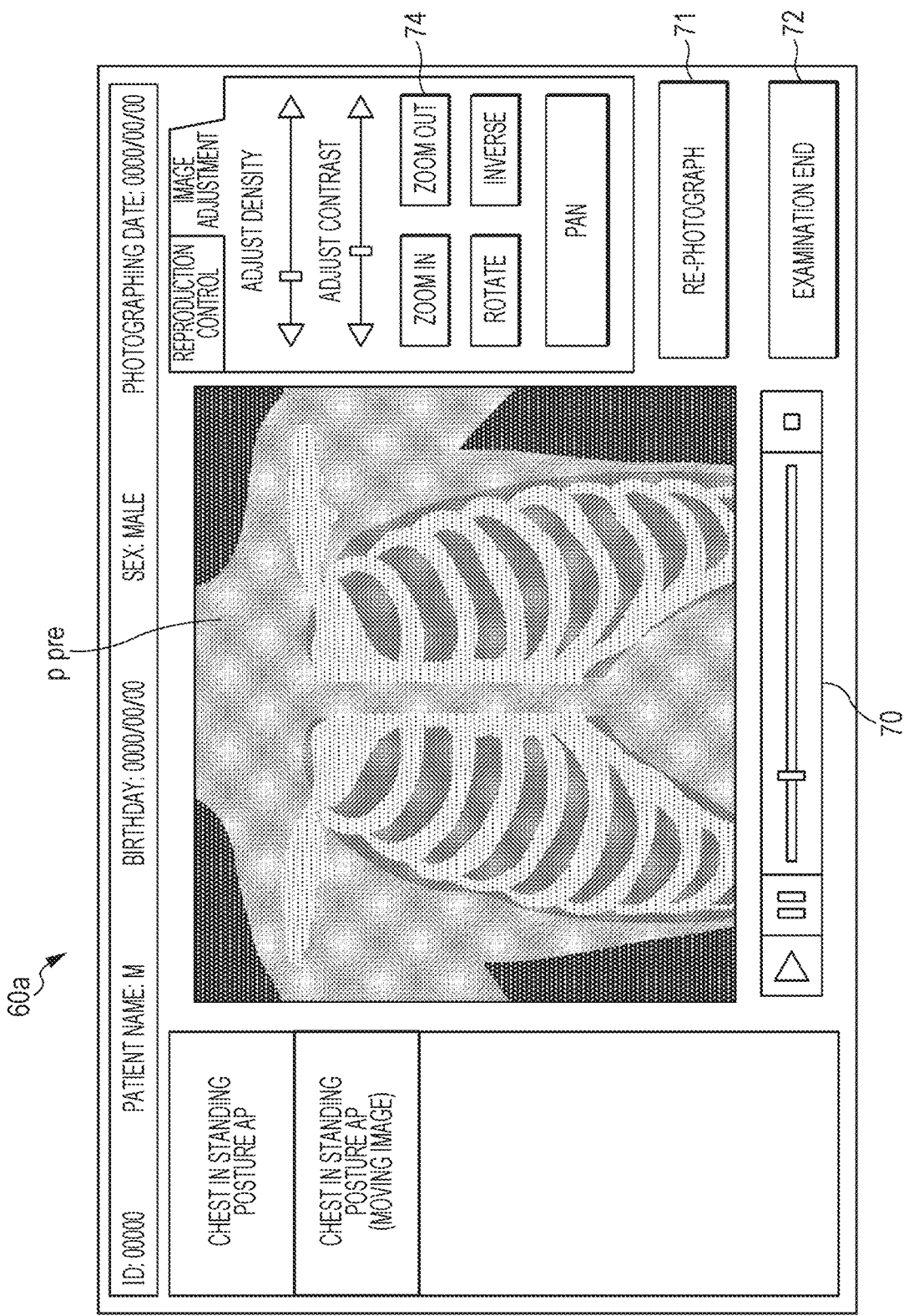
FIG. 10 is a view illustrating another example of a display screen displayed on the display of the radiation image display apparatus, and illustrating a case where a screen for image adjustment is displayed according to one or more embodiments of the invention.

When the screen is switched to the screen adjustment screen using the tabs, various icons 74 for image adjustment, that is, icons 74 for density adjustment, contrast adjustment, zoom in, zoom out, rotation, inversion, and panning, are displayed on the right side of the screen as illustrated in FIG. 10. Then, the photographer can input an instruction to perform each process of density adjustment, contrast adjustment, zoom in/zoom out, rotation/inversion, and panning by clicking these icons 74 or sliding slider bars.

Then, when the photographer instructs the image adjustment by clicking the icons 74 or the like (Yes in step S11), the image adjuster 65 of the radiation image display apparatus 60 performs the image adjustment according to the instruction by the photographer (that is, density adjustment, etc.) (step S12).

In the above description, the image adjuster 65 performs the image adjustment such as density adjustment according to input of a user such as a radiological technician. However, a way of image adjustment can be previously set in the image adjuster 65, and the image adjuster 65 can be configured to perform the image adjustment including one or more of density adjustment, contrast adjustment, zoom in/zoom out, panning, and rotation/inversion on the preview images ppre according to the preset way.

Then, the display unit 63 of the radiation image display apparatus 60 is configured to display the preview images ppre on the display 60a after image adjustment such as density adjustment by the image adjuster 65.

Also, in one or more embodiments, when the photographer who has viewed the preview images ppre, and performed reproduction control and image adjustment determines that re-photographing of the image is necessary because an object is not properly photographed or the like as a result of the image check, the photographer can input an instruction of re-photographing an image to the radiation image display apparatus 60 by clicking the re-photograph icon 71 in the lower right part of the display screen.

Figure 11:
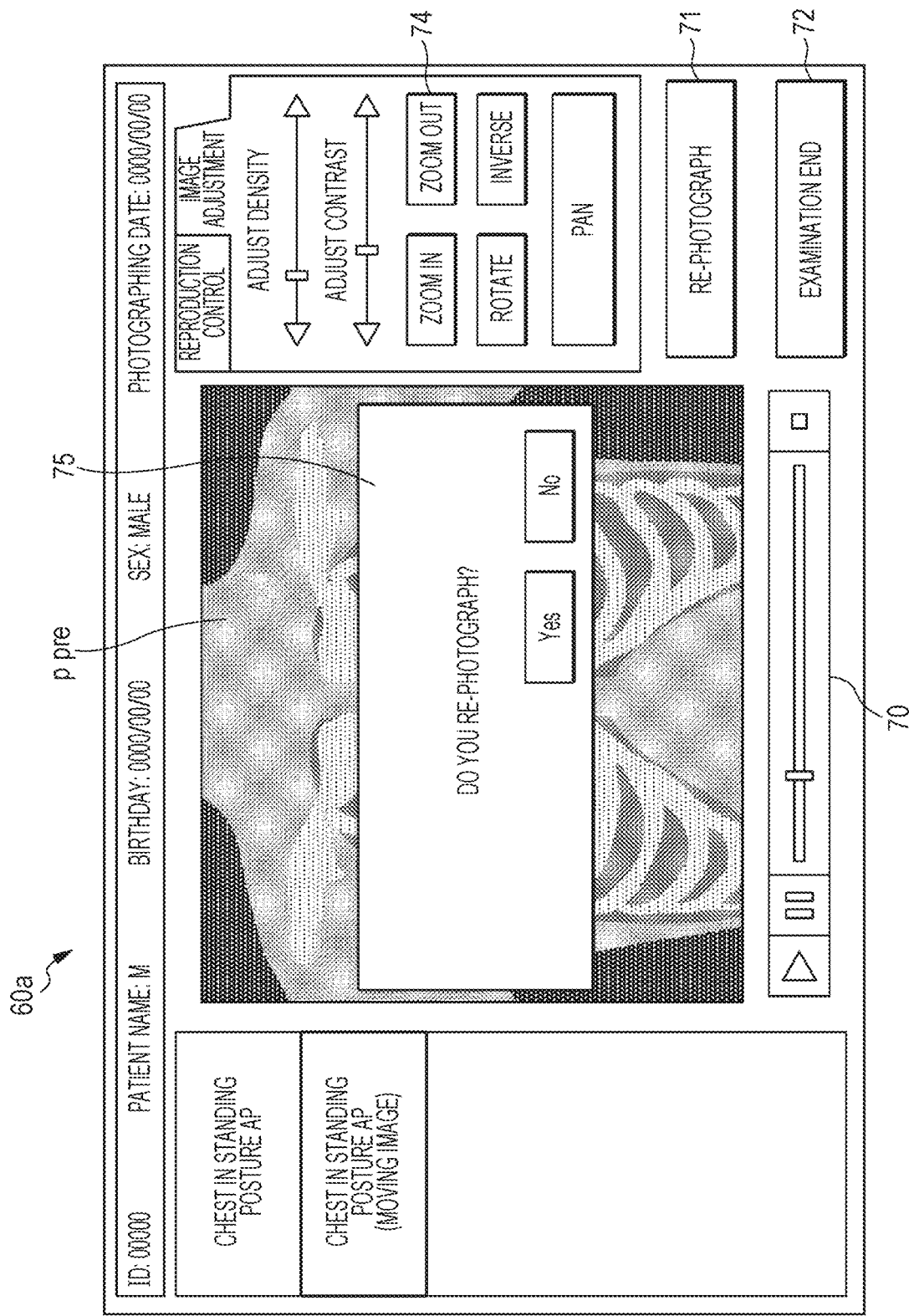
FIG. 11 is a diagram illustrating an example of a confirmation display for asking whether re-photographing should be performed according to one or more embodiments of the invention.
Figure 12:
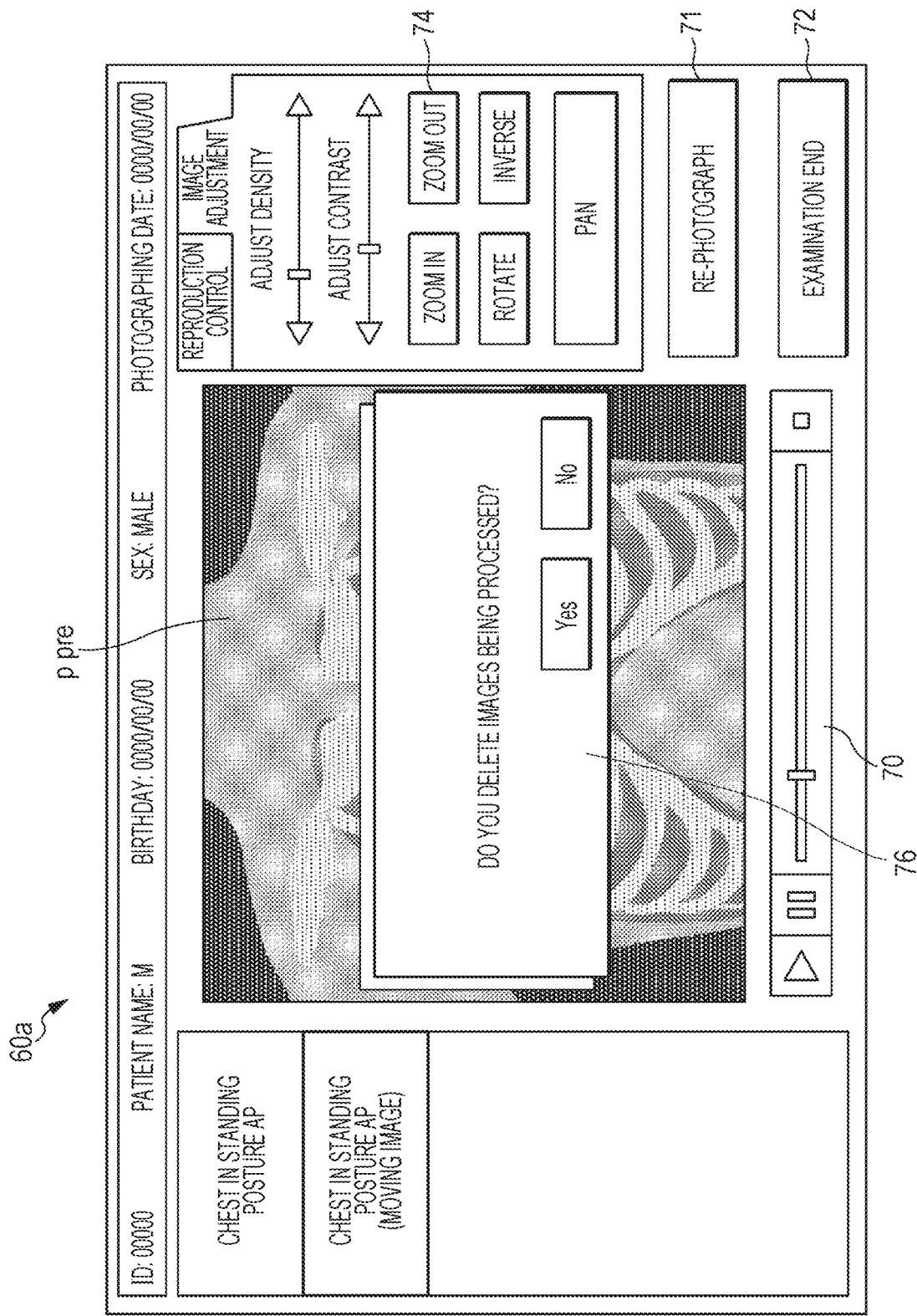
FIG. 12 is a diagram illustrating an example of a confirmation display for asking whether an image being processed should be deleted according to one or more embodiments of the invention.
Figure 13:
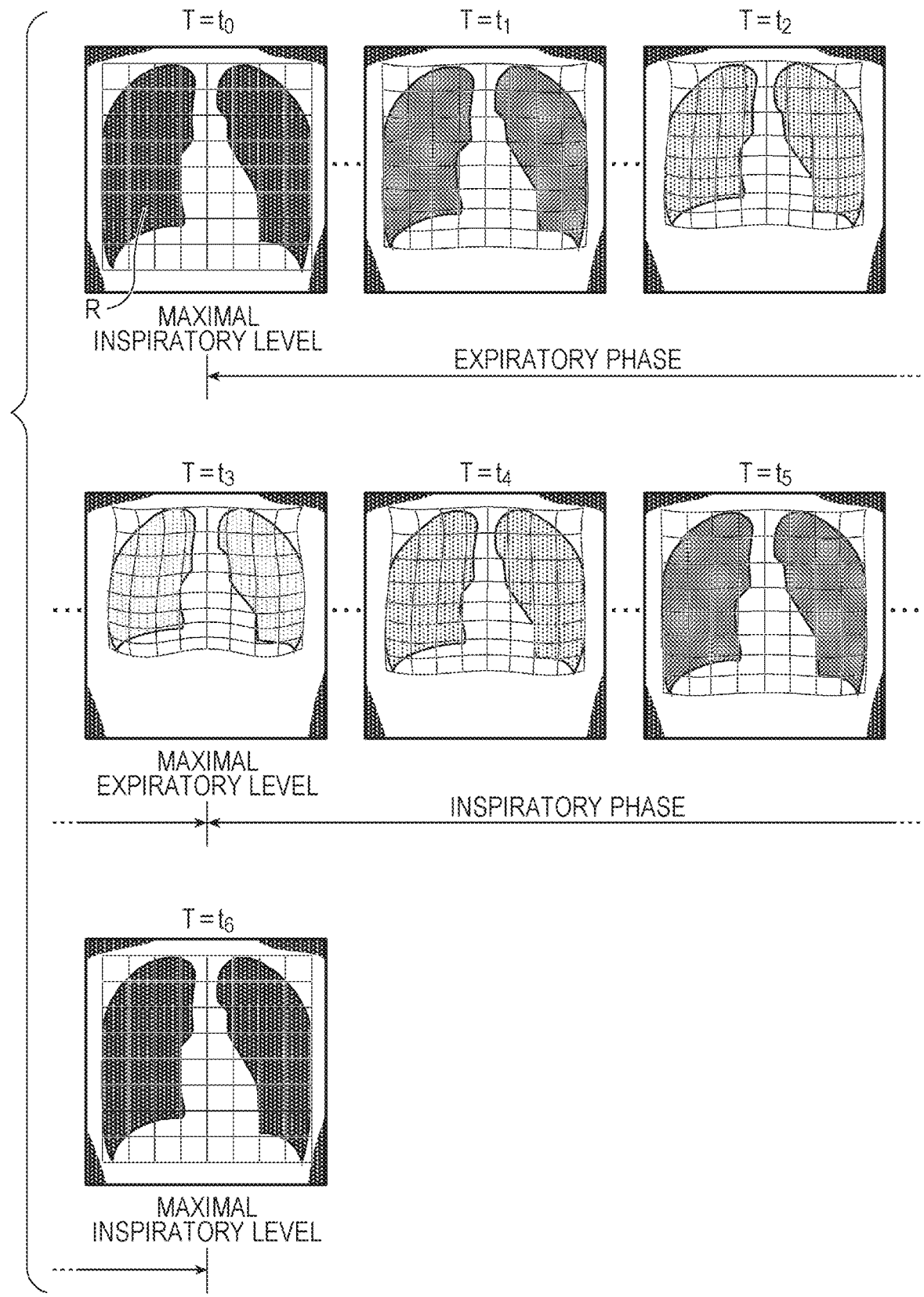
FIG. 13 is a view illustrating an example of frame images photographed by dynamic photographing of the chest of a patient according to one or more embodiments of the invention.

Then, when the photographer clicks the re-photograph icon 71 to input an instruction for re-photographing to the display unit 63 of the radiation image display apparatus 60 (Yes in step S13), the display unit 63 displays confirmation display 75 to confirm that re-photographing should be performed as illustrated in FIG. 11. Then, when the "Yes" icon is clicked, in one or more embodiments, the display unit 63 subsequently displays confirmation display 76 to confirm whether to delete data such as image data D (image data D, main image p, preview images ppre) that is stored by the generator 61 and related to the images currently being processed as illustrated in FIG. 12.

A photographer may determine that re-photographing of an image is necessary in various cases such as a case where an object does not appear in preview images ppre, a case where the irradiation dose is obviously inappropriate, or body movement occurs. In addition, a photographer may determine that re-photographing of an image should be performed just in case even though a moving image is appropriately photographed to some extent. In the former case, there is no point in keeping the image data D and the like in which the object is not photographed, so that the image data D and the like are deleted. However, in the latter case, if the photographer determines that there is a possibility that the photographed result of re-photographing will be bad and the photographer will want to use the image data D or the like of the previously photographed moving image, the photographer selects not to delete on the confirmation display 76.

Therefore, when the radiation image display apparatus 60 is instructed to delete the images through the above confirmation display 76 (Yes in step S14), the radiation image display apparatus 60 deletes data related to the images currently being processed (step S15). The radiation image display apparatus 60 may be configured to preset which of image data D, main image p, and preview images ppre should be deleted and which of them should be kept stored, or all of them should be deleted, or to allow a photographer to select from such options.

When the radiation image display apparatus 60 is instructed not to delete the image through the confirmation display 76 (No in step S14), the radiation image display apparatus 60 stores the data related to the images currently being processed in the storage 60c (refer to FIG. 3) (step S16). The radiation image display apparatus 60 can also be configured to keep whole data related to the images currently being processed by the radiation image display apparatus 60 without asking a photographer when re-photographing is performed. Thus, whether the data should be deleted or kept stored may be appropriately determined.

Moving image photographing for the re-photographing is then started (step S1) and the above described processes are also performed on the moving image photographing for the re-photographing. When all the processes end and a photographer clicks the examination end icon 72 (Yes in step S17), the radiation image display apparatus 60 ends the processes.

[Effect]

As described above, according to the radiation image display apparatus 60 and the radiation image photographing system 100 according to one or more embodiments, when a piece of image data D is transferred from the radiation image photographing apparatus 1 to the radiation image display apparatus 60 for each frame, the radiation image display apparatus 60 generates a preview image ppre (a moving image for preview ppre) based on the piece of the image data D and displays the generated preview image ppre on the display 60a, the radiation image display apparatus 60 also allows a photographer such as a radiological technician to perform reproduction control or image adjustment on the preview image ppre without need to wait for generation of a main image p (a moving image p as a main image), so that early image check is possible.

Therefore, the radiation image display apparatus 60 and the radiation image photographing system 100 are easy to use and excellent in operability for a photographer. Also, while a patient as an object waits for image check, the patient has to wait in the posture as he/she is. According to the radiation image display apparatus 60 and the radiation image photographing system 100 according to one or more embodiments, early image check is possible as described above, which shortens waiting time of the patient and thus reduces the burden on the patient.

Especially, in a case where the radiation image display apparatus 60 is mounted on the visiting car 80 (refer to FIG. 4) or the radiation image display apparatus 60 is portable terminal type that is carried by a photographer (refer to FIG. 5), the performance may not be so high and the processing speed may not be so fast. In such a case, the time from the start of moving image photographing to the time when a main image p is generated and displayed may become significantly long. In such a case, if the image can not be checked until the main image p is displayed and thus the patient must wait in the same posture, the burden on the patient becomes significantly high. However, such a situation does not occur with the radiation image display apparatus 60 and the radiation image photographing system 100 according to one or more embodiments, and the waiting time of the patient can be shortened as described above, and thus the burden on the patient can be significantly reduced.

Meanwhile, when there are a large number of objects to be photographed and it is necessary to repeat moving image photographing many times, for example, in group examination, the time from the start of the group examination to the end thereof is significantly long if image check is not possible and an object to be photographed cannot be changed until a main image p is displayed. Thus, the time taken by photographing one person is increased, and the time from the start of group examination to the end thereof is long. However, with the radiation image display apparatus 60 and the radiation image photographing system 100 according to one or more embodiments, the waiting time of a person to be photographed can be shortened as described above, and the time taken for photographing a moving image of one person to be photographed is reduced, and thus the time taken by group examination can be significantly reduced.

In one or more embodiments, pieces of the image data D are transferred for respective frames from the radiation image photographing apparatus 1 to the radiation image display apparatus 60, and the radiation image display apparatus 60 extracts frames at a predetermined ratio for preview images ppre, or extracts parts from the image data D for preview images ppre at a predetermined ratio. Alternatively, the radiation image photographing apparatus 1 and the radiation image display apparatus 60 can be configured such that when the radiation image photographing apparatus 1 transfers the image data D to the radiation image display apparatus 60, the radiation image photographing apparatus 1 extracts and transfers frames at a predetermined ratio, or extracts and transfers parts of the image data D for preview images ppre at a predetermined ratio.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A radiation image display apparatus comprising:
   a hardware processor configured to generate preview images for preview based on image data of a plurality of frames obtained by dynamic photographing of an object via detection of radiation, wherein the preview images are generated while the dynamic photographing of the object is performed; and
   a holder that stores the preview images, wherein
   the hardware processor is further configured to:
      display the preview images on a display during dynamic photographing of the object,
      perform reproduction control including one or more of:
         playback,
         reverse playback,
         stop,
         fast forward,
         rewind,
         frame feed,
         frame rewind, and
         repeat playback
      on the preview images, and
      display the preview images according to the reproduction control, and
   the preview images show moving images of the object.

2. The radiation image display apparatus according to claim 1, wherein the hardware processor is further configured to:
   extract frames from the plurality of frames at a predetermined ratio,
   generate the preview images based on image data of the extracted frames, and
   change the predetermined ratio according to a transfer speed when the image data are transferred.

3. The radiation image display apparatus according to claim 1, wherein the hardware processor is further configured to:
   extract a part of the image data from the image data for each frame of the plurality of frames at a predetermined ratio, and
   generate the preview images based on the part of the extracted image data.

4. The radiation image display apparatus according to claim 1, wherein the hardware processor is further configured to generate the preview images by performing image processing that is simpler than image processing performed to generate main images based on the image data of the plurality of frames.

5. The radiation image display apparatus according to claim 1, wherein one or more instructions of:
   playback,
   reverse playback,
   stop,
   fast forward,
   rewind,
   frame feed,
   frame rewind, and
   repeat playback
are input into the hardware processor.

6. The radiation image display apparatus according to claim 5, wherein the instructions are input into the hardware processor using mouse operation, touch panel operation, or operation by a gesture of a user.

7. The radiation image display apparatus according to claim 1, wherein the hardware processor is further configured to perform image adjustment including one or more of:
   density adjustment,
   contrast adjustment,
   zoom in/zoom out,
   panning, and
   rotation/inversion
on the preview images for preview according to a preset method.

8. The radiation image display apparatus according to claim 1, wherein one or more instructions of:
   density adjustment,
   contrast adjustment,
   zoom in/zoom out,
   panning, and
   rotation/inversion
are input into the hardware processor.

9. The radiation image display apparatus according to claim 8, wherein the instructions are input into to the hardware processor using mouse operation, touch panel operation, or operation by a gesture of a user.

10. The radiation image display apparatus according to claim 1, wherein a re-photographing instruction to photograph the object via detection of radiation is input into the hardware processor by operation of a user.

11. The radiation image display apparatus according to claim 10, wherein, when the hardware processor is further configured to receive the re-photographing instruction, the radiation image display apparatus displays a message indicating whether the image data stored by the hardware processor should be deleted.

12. The radiation image display apparatus according to claim 10, wherein whether the image data stored by the hardware processor is deleted or kept stored when the re-photographing instruction is received is previously set.

13. The radiation image display apparatus according to claim 1, wherein the hardware processor is further configured to generate main images based on the image data of the plurality of frames after generating the preview images.

14. The radiation image display apparatus according to claim 13, wherein upon generation of the main images by the hardware processor, the hardware processor is further configured to display the main images on the display instead of the preview images.

15. A radiation dynamic image photographing system comprising:
   the radiation image display apparatus according to claim 1;

a radiation irradiation apparatus that irradiates the object with radiation; and a radiation dynamic image photographing apparatus that reads radiation through the object as the image data for each of the plurality of frames and transfers the image data to the radiation image display apparatus.

16. A radiation image display apparatus comprising:
a hardware processor configured to generate preview images for preview based on image data of a plurality of frames obtained by dynamic photographing of an object via detection of radiation, wherein the preview images are generated while the dynamic photographing of the object is performed; and
a holder that stores the preview images, wherein
the hardware processor is further configured to:
   perform image adjustment on the preview images,
   display the preview images on a display during dynamic photographing of the object,
   perform reproduction control including one or more of:
      playback,
      reverse playback,
      stop,
      fast forward,
      rewind,
      frame feed,
      frame rewind, and
      repeat playback
   on the preview images, and
   display the preview images according to the reproduction control and display the preview images subjected to the image adjustment on the display, and
the preview images show moving images of the object.

17. A radiation image display apparatus comprising:
a hardware processor configured to:
   generate preview images for preview based on image data of a plurality of frames obtained by dynamic photographing of an object via detection of radiation, wherein the preview images are generated and stored while the dynamic photographing of the object is performed,
   display the preview images on a display before an end of irradiation for dynamic photographing of the object,
   perform reproduction control including one or more of:
      playback,
      reverse playback,
      stop,
      fast forward,
      rewind,
      frame feed,
      frame rewind, and
      repeat playback
   on the preview images, and
   display the preview images according to the reproduction control on the display, wherein
the preview images show moving images of the object.

18. A radiation image display apparatus comprising:
a hardware processor configured to:
   extract frames at a predetermined ratio from a plurality of frames obtained by dynamic photographing of an object via detection of radiation;
   generate preview images for preview based on image data of the extracted frames wherein the preview images are generated and stored while the dynamic photographing of the object is performed,
   display the preview images on a display at a preview frame rate that is lower by the predetermined ratio than an imaging frame rate of dynamic photographing of the object,
   perform reproduction control including one or more of:
      playback,
      reverse playback,
      stop,
      fast forward,
      rewind,
      frame feed,
      frame rewind, and
      repeat playback
   on the preview images, and
   display the preview images according to the reproduction control on the display, wherein
the preview images show moving images of the object.

19. A radiation image display apparatus comprising:
a hardware processor configured to:
   extract frames at a predetermined ratio from a plurality of original frames obtained by dynamic photographing of an object via detection of radiation and generate preview images based on image data of the extracted frames, wherein the preview images are generated and stored while the dynamic photographing of the object is performed,
   display the preview images on a display during dynamic photographing of the object,
   perform reproduction control including one or more of:
      playback,
      reverse playback,
      stop,
      fast forward,
      rewind,
      frame feed,
      frame rewind, and
      repeat playback
   on the preview images, and
   display the preview images according to the reproduction control on the display, wherein
the preview images show moving images of the object.

* * * * *